(12) United States Patent
Opsahl et al.

(10) Patent No.: US 10,278,945 B2
(45) Date of Patent: May 7, 2019

(54) FORMULATION FOR THE TREATMENT OF ACNE

(71) Applicant: Akzo Nobel Chemicals International B.V., Arnhem (NL)

(72) Inventors: Ross Christian Opsahl, Geneva, IL (US); Steluta Gina Butuc, The Woodlands, TX (US)

(73) Assignee: Akzo Nobel Chemicals International B.V., Arnhem (NL)

( * ) Notice: Subject to any disclaimer, the term of this patent is extended or adjusted under 35 U.S.C. 154(b) by 0 days.

(21) Appl. No.: 15/755,586

(22) PCT Filed: Aug. 25, 2016

(86) PCT No.: PCT/EP2016/070036
§ 371 (c)(1),
(2) Date: Feb. 27, 2018

(87) PCT Pub. No.: WO2017/036897
PCT Pub. Date: Mar. 9, 2017

(65) Prior Publication Data
US 2019/0022050 A1    Jan. 24, 2019

Related U.S. Application Data

(60) Provisional application No. 62/211,060, filed on Aug. 28, 2015.

(30) Foreign Application Priority Data

Oct. 2, 2015 (EP) .................................... 15188210

(51) Int. Cl.
    *A61K 31/327*    (2006.01)
    *A61K 9/06*     (2006.01)
    (Continued)

(52) U.S. Cl.
    CPC .......... *A61K 31/327* (2013.01); *A61K 9/0014* (2013.01); *A61K 9/06* (2013.01); *A61K 47/36* (2013.01); *A61P 17/10* (2018.01)

(58) Field of Classification Search
    None
    See application file for complete search history.

(56) References Cited

FOREIGN PATENT DOCUMENTS

DE       298 591 A5    3/1992
EP    0 017 151 A2    10/1980
(Continued)

OTHER PUBLICATIONS

Database CAPLUS Chemical Abstracts Service, Columbus, Ohio, US; Database Accession No. 1992:250511, Abstract of DD 298591, Brueckner et al. Mar. 5, 1992 (Year: 1992).*

(Continued)

*Primary Examiner* — Karl J Puttlitz
(74) *Attorney, Agent, or Firm* — Matthew D. Kellam

(57) ABSTRACT

Peroxide of the formula wherein $R^1$ is selected from linear and branched alkyl groups with 1-4 carbon atoms, and $R^2$, $R^3$, and $R^4$ are selected from hydrogen and linear and branched alkyl groups with 1-4 carbon atoms, for use as a medicament, in particular for the treatment of acne.

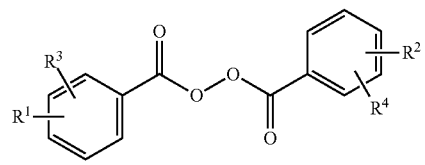

7 Claims, 3 Drawing Sheets

Figure 1:
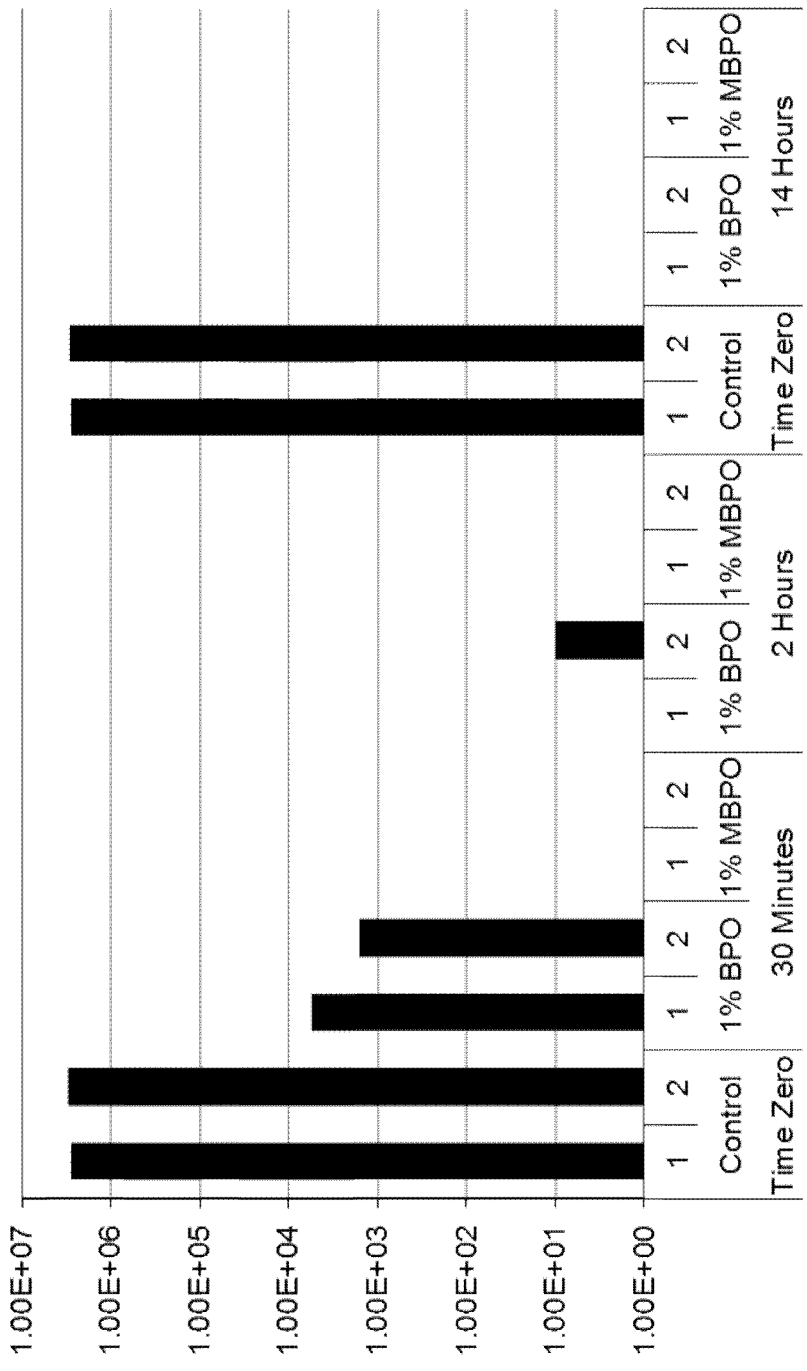

(51) Int. Cl.
*A61P 17/10* (2006.01)
*A61K 47/36* (2006.01)
*A61K 9/00* (2006.01)

(56) References Cited

FOREIGN PATENT DOCUMENTS

| GB | 2 196 339 A | | 4/1988 |
|----|-------------|---|--------|
| WO | 2011/117870 A2 | | 9/2011 |
| WO | 2011117870 | * | 9/2011 |

OTHER PUBLICATIONS

European Search Report issued in the counterpart European Application No. 15188210.7 dated Feb. 1, 2016.
Notification of Transmittal of the International Search Report and Written Opinion of the International Searching Authority, or the Declaration from the International Bureau of WIPO for International Application No. PCT/EP2016/070036 dated Oct. 28, 2016.

* cited by examiner

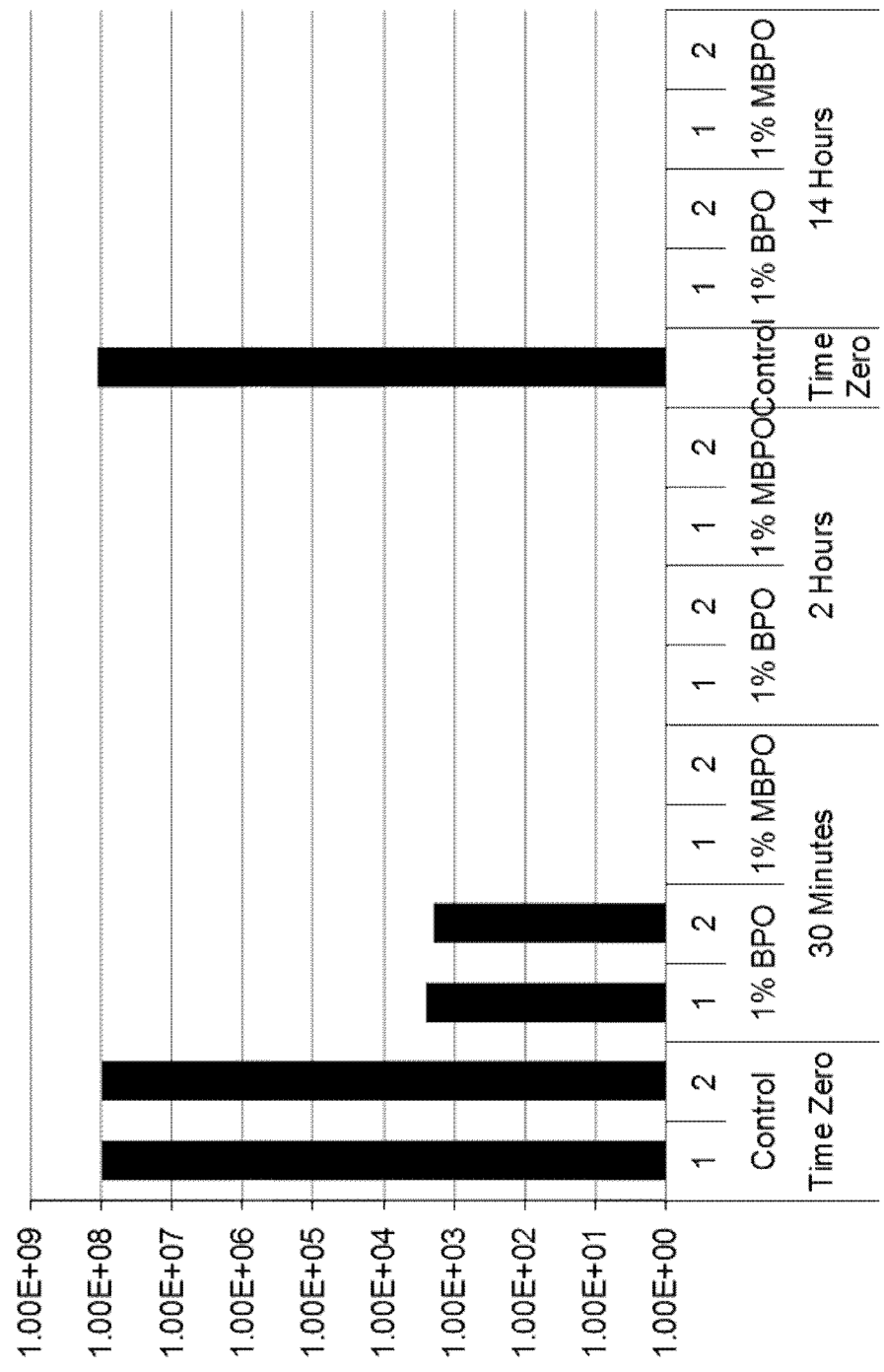

FORMULATION FOR THE TREATMENT OF ACNE

This application is a national stage filing under 35 U.S.C. § 371 of PCT/EP2016/070036, filed Aug. 25, 2016, which claims priority to U.S. Provisional Patent Application No. 62/211,060 filed Aug. 28, 2015, and European Patent Application No. 15188210.7, filed Oct. 2, 2015, the contents of which are each incorporated herein by reference in their entireties.

The present invention relates to an organic peroxide for the treatment of acne and a skin treatment formulation comprising this organic peroxide.

Acne vulgaris is a chronic disorder of the pilosebaceous follicles (apparati) which is characterized by comedones (blackheads), papules, pustules, cysts, nodules and often scars which appear in the most visible regions of the skin, in particular the face, chest, back and sometimes the neck and top of the arms. Acne affects 90% of all adolescents and many men and women of older age.

Acne is caused by bacteria, such as *Staphylococcus aureus* (ATCC 6538), *Staphylococcus epidermidis* (ATCC 12228), and *Propionibacerium acnes* (ATCC 6919).

Dibenzoyl peroxide is a well-known active ingredient in formulations for the treatment of acne. It is able to inhibit the proliferation of the above-mentioned bacteria.

Surprisingly, it has now been found that substitution of dibenzoyl peroxide with alkyl or alkoxy groups results in an even better anti-microbial activity against these bacteria.

The present invention therefore relates to a the use of a peroxide with the formula

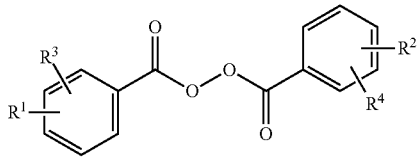

wherein $R^1$ is selected from linear and branched alkyl groups with 1-4 carbon atoms, and $R^2$, $R^3$, and $R^4$ are selected from hydrogen and linear and branched alkyl groups with 1-4 carbon atoms, for killing and/or inhibiting the proliferation of *Staphylococcus aureus* (ATCC 6538), *Staphylococcus epidermidis* (ATCC 12228), and *Propionibacerium acnes* (ATCC 6919), and, consequently, for the treatment of acne.

The invention also relates to a skin-treatment formulation which comprises said peroxide, water, and a dispersant system.

In a preferred embodiment, $R^1$ and $R^2$ are both methyl groups, both tertiary butyl groups, or n-butyl groups, whereas $R^3$ and $R^4$ are preferably hydrogens. In an even more preferred embodiment, $R^1$ and $R^2$ are both positioned at the para-position.

In a most preferred embodiment, the peroxide is di(4-methylbenzoyl) peroxide.

The peroxide is solid at room temperature and has the form of particles.

In a preferred embodiment, 99% of the peroxide particles (d99) have a diameter or less than 75 microns, more preferably less than 50 microns, more preferably less than 25 microns, even more preferably less than 10 microns, and most preferably less than 5 microns. The particles are preferably larger than 0.1 microns, most preferably larger than 0.5 microns.

The particle size is measured using laser light diffraction of an aqueous peroxide suspension according to NEN-ISO 13320-1, after 10 minutes of ultrasonication to de-agglomerate the sample.

Such peroxide particle sizes can be obtained by wet grinding the peroxide, either before or after it has been introduced into the skin-treatment formulation.

The skin-treatment formulation can have the form of a cream, gel, or lotion, or any other form that may allow application to the skin. The peroxide, which is typically solid at room temperature, is present in said formulation as solid particles.

The dispersant system serves to stabilize the peroxide-in-water suspension. The dispersant system contains at least one compound selected from suspending agent(s), gelling aid(s), buffering agent(s), defoamer(s), and dispersant(s). These compounds should be non-reactive with respect to the peroxide and non-toxic and therefore safe for topical application.

Suitable suspending agents include acrylate copolymers, acrylate/methoxy peg-15 methacrylate copolymer, acrylate/steareth-20 methacrylate crosspolymer, acrylate/vinyl isodecanoate crosspolymer, acrylate/vp copolymer, acrylic acid/acrylamidomethyl propane sulfonic acid copolymer, acrylic acid/vp crosspolymer, ammonium styrene/acrylates copolymer, ammonium vinyl acetate/acrylates copolymer, bentonite, biotite, butyl babassuate, calcium lignosulfonate, C4-24 alkyl dimethicone/divinyldimethicone crosspolymer, chitosan lauramide succinamide, coralline *officinalis* powder, corn starch/acrylamide/sodium acrylate copolymer, dehydroxanthan gum, diallyloxyneohexyl zirconium tridecanoate, dehydrogenated tallow benzylmonium hectorite, dimethicone crosspolymer, dimethiconol/stearyl methicone/phenyl trimethicone copolymer, dimethylol urea/phenol/sodium phenolsulfonate copolymer, dipentaerythityl pentaisostearate, disodium methylene dinaphthalenesulfonate, disteardimonium hectorite, ditrimethylol propane isostearate/sebacate, ditrimethylol propane triethylhexanoate, erythityl triethylhexanoate, ethylene/ma copolymer, ethylene/va copolymer, ethylhexyl hydroxystearoyl hydroxystearate, ethyl trisiloxane, feruloyl soy glycerides, glass, glass beads, hectorite, hydrogenated isocetyl olivate, hydrogenated lecithin, hydroxyethyl acrylate/sodium actyloyldimethyl taurate copolymer, hydroxyethyl pei-1000, hydroxyethyl pei-1500, hydroxypropyl starch, hydroxypropyltrimonium maltodextrin crosspolymer, isobutylene/ma copolymer, isopropyl babassuate, isopropyl ester of pvm/ma copolymer, magnesium phosphate, maltodextrin, methacrylol ethyl betaine/acrylates copolymer, methoxy peg-17/dodecyl glycol copolymer, methoxy peg-22/dodecyl glycol copolymer, methoxy peg-114/polyepsilon caprolactone, methyl methacrylate, myristoyl/pca chitin, nitrocellulose, octyldodecyl/ppg-3 myristyl ether dimmer dilinoleate, peg-18 castor oil dioleate, peg-150/decyl alcohol/smdi copolymer, peg-12 dimethicone crosspolymer, peg-150 stearyl alcohol/smdi copolymer, pei-7, pei-10, pei-15, pei-30, pei-35, pei-45, pei-250, pei-275, pei-700, pei-1000, pei-1400, pei-1500, pei-1750, pei-2500, pei-14m, pentafluoropropane, perfluoronyl octyldodecyl glycol meadowfoamate, perlite, phosphonobutanetricacarboxylic acid, polyacrylamidomethylpropane sulfonic acid, polyacrylate-10, polyacrylate-11, polycaprolactone, polyethyl acrylate, polyglyceryl-4 isostearate/laurate, polyhydroxystearic acid, polyxymethylene cyanoguanidine urea, polyperfluorethoxymethoxy peg-2 phosphate, polyvinyl imidazolinium acetate, polyvinyl methyl ether, ppg-3 myristyl ether neoheptanoate, propylene glycol ricinoleate, pvm/ma copolymer, pvp, pvp/va/ltaconic acid copolymer, quaternium-18 bentonite, quaternium-18/benzalkonium bentonite, quaternium-18 hectorite, quaternium-90 bentonite, rhizobian gum, silica, silica dimethicone silylate, silica dimethylsilylate, silica silylate, sodium acrylate/sodium acryloyldimethyl taurate/acrylamide copolymer, sodium acrylates/vinyl isodecanoate crosspolymer, sodium acrylates/vinyl isodecanoate crosspolymer, sodium acrylic acid/macopolymer, sodium acryloyldimethyl taurate/acrylamide/vp copolymer, sodium $C_{4-12}$ olefin/maleic acid copolymer, sodium dextran sulfate, sodium dimaltodextrin phosphate, sodium glycereth-1 polyphosphate, sodium isooctylene/macopolymer, sodium magnesium fluorosilicate, starch hydroxypropyltrimonium chloride, stearalkonium bentonite, stearalkonium hectorite, stearyl/ppg-3 myristyl ether dimmer dilinoleate, stearylvinyl ether/ma copolymer, styrene/acrylates/acrylonitrile copolymer, styrene/acrylates/ammonium methacrylate copolymer, styrene/ma copolymer, sucrose benzoate/sucrose acetate isobutyrate/butyl benzyl phthalate copolymer, synthetic ruby, synthetic ruby powder, tosylamide/epoxy resin, tosylamide/formaldehyde resin, tribenzoyl triricinolein, vp/dimethylaminoethylmethacrylate copolymer, vp/eicosene copolymer, vp/hexadecene copolymer, and vp/va copolymer.

Suitable gelling agents include alcohol, denaturated alcohol, benzyl alcohol, 1,2-butanediol, butoxydiglycol, butoxyethanol, butylene glycol, cd alcohol 19, ceteareth-22, $C_{7-8}$ isoparaffin, $C_{8-9}$ isoparaffin, $C_{9-11}$ iso-paraffin, $C_{9-13}$ isoparaffin, $C_{9-14}$ isoparaffin, $C_{10-11}$ isoparaffin, $C_{10-12}$ isoparaffin, $C_{11-14}$ isoparaffin, decane, decene, deodorized kerosene, diethylene glycol, dimethyl ether, dimethyl isosorbide, dimethyl sulfone, dipropylene glycol, dodecene, ethoxydiglycol, ethoxyethanol, ethyl perfluorobutyl ether, ethyl perfluoroisobutyl ether, ethyl trisiloxane, glycereth-7, glycereth-8, glycereth-12, glycereth-20, glycereth-26, glycereth-31, glycerin, glycofurol, glycol, heptane, hexadecene, hexane, 1,2,6-hexanetriol, hexyl alcohol, hexylene glycol, isobutoxypropanol, isopentane, isopropyl alcohol, methoxydiglycol, methoxyethanol, methoxyethanol acetate, methoxyisopropanol, methyl hexyl ether, methyl perfluorobutyl ether, methyl perfluoroisobutyl ether, octadecene, octane, pentane, polyglyceryl sorbitol, propanediol, propyl alcohol, propylene carbonate, propylene glycol, sd alcohol 1, sd alcohol 3-a, sd alcohol 3-b, sd alcohol 3-c, sd alcohol 23-a, sd alcohol 23-f, sd alcohol 23-h, sd alcohol 27-b, sd alcohol 30, sd alcohol 31-a, sd alcohol 36, sd alcohol 37, sd alcohol 38-b, sd alcohol 38-c, sd alcohol 38-d, sd alcohol 38-f, sd alcohol 39, sd alcohol 39-a, sd alcohol 39-b, sd alcohol 39-c, sd alcohol 39-d, sd alcohol 40, sd alcohol 40-1, sd alcohol 40-b, sd alcohol 40-c, sd alcohol 46, sorbeth-6, sorbeth-30, sorbeth-40, tetradecene, and triethylene glycol, turpentine.

Suitable defoamers include alcohol, denaturated alcohol, behenyl methacrylate/ethylamine oxide, methacrylate copolymet, bisphenylhexamethicone, cetyl dimethicone, c12-14 sec-pareth-5, dimethicone, dimethicone silylate, dimethiconol, diphenyl dimethicone, diphenylsiloxy phenyl trimethicone, disiloxane, fluoro c2-8 alkyldimethicone, hexadecyl methicone, hexyl alcohol, isopropyl alcohol, laureth-5 butyl ether, peg/ppg-8/26 dimethicone, peg/ppg-12/16 dimethicone, peg/ppg-12/18 dimethicone, peg/ppg-16/8 dimethicone, petroleum distillates, phenethyl disiloxane, phenyl dimethicone, phenyl trimethicone, polysilicone-1, polysilicone-2, polysilicone-7, polysilicone-8, polysilicone-10, propyl alcohol, silica dimethicone silylate, silica silylate, dimethicone, trimethylsiloxysilicate, trimethylsiloxysilicate/dimethicone crosspolymer, triphenyl trimethicone, and trisiloxane.

Suitable buffering agents include aluminum glycinate, aluminum lactate, ammonium acetate, ammonium carbonate, ammonium hexafluorophosphate, ammonium lactate, ammonium molybdate, ammonium phosphate, ammonium vanadate, boric acid, calcium carbonate, calcium phosphate, clay minerals, cyclohexylamine, decapeptide-7, diammonium citrate, diammonium phosphate, diethanolamine bisulfate, diethylamine, diethyl ethanolamine, disodium fumarate, disodium phosphate, disodium pyrophosphate, ectoin, ethanolamine hcl, glycine, hydroxyethylpiperazine ethane sulfonic acid, lauryl p-cresol ketoxime, lithium fluoride, magnesium acetate, magnesium lactate, mes-borate, methoxy peg-114/polyepsilon caprolactone, mipa-borate, phosphonobutanetricarboxylic acid, potassium acetate, potassium bicarbonate, potassium biphthalate, potassium citrate, potassium lactate, sodium acetate, sodium aluminate, sodium aluminum lactate, sodium bicarbonate, sodium citrate, sodium fumarate, sodium humate, sodium lactate, sodium phosphate, sodium silicate, sodium succinate, sodium trimetaphosphate, tetrapotassium pyrophosphate, tetrasodium pyrophosphate, trisodium sulfosuccinate, urea, zinc glycinate, and zinc hexametaphosphate.

Suitable dispersants include cellulosic derivatives and surfactants, including both anionic surfactants and nonionic surfactants, inorganic colloidal materials, and carboxyvinyl polymers (Carbomer). The dispersant may comprise cellulose ethers and cellulose esters such as carboxymethyl cellulose, hydroxyethyl cellulose, or hydroxypropylmethyl-cellulose; polysaccharide gums such as xanthan gums, guar gums, carrageenan gum, modified starches such as the modified potato starch and the like, polyacrylamides such as polyacrylamide/$C_{13-14}$ isoparaffin/laureth-7 mixture, a mixture of sodium acryloyldimethyltaurate copolymer/isohexadecane/polysorbate 80; acrylic polymers coupled to hydrophobic chains, such as the PEG-150/decyl/SMDI copolymer, aluminum/magnesium silicate, polyvinyl alcohol, polyethylene oxides, propylene glycol alginates or mixtures thereof.

Particularly preferred dispersants are 1,3 propanediol and sodium dioctyl sulfosuccinate.

The pH of the skin-treatment formulation according to the present invention is preferably in the range 2.8 to 6.6, more preferably 5.5 to 6.0.

The peroxide concentration in the skin-treatment formulation according to the present invention is preferably at least 0.1 wt %, more preferably at least 0.5 wt %, even more preferably at least 1 wt %, and most preferably at least 5 wt %. The peroxide concentration is preferably below 20 wt %, more preferably below 15 wt %.

FIGURES

The figures display the number of colony forming units (CFU) per ml, 30 minutes, 2 hours, and 14 hours after contacting different bacteria with 1% dibenzoyl peroxide (BPO) and 1% di(4-methylbenzoyl) peroxide (MBPO) formulations.

Bacteria used were: *Staphylococcus aureus* (FIG. 1) *Staphylococcus epidermidis* (FIG. 2), and *Propionibacerium acnes* (FIG. 3).

EXAMPLES

Two formulations were prepared:
a suspension of 1 wt % dibenzoyl peroxide (BPO) in water a suspension of 1 wt % di(4-methybenzoyl) peroxide (MBPO) in water The BPO-suspension was prepared by:
mixing 0.4 g of food-grade xanthan gum into 39.6 g of demineralized water until it was lump free,
dissolving BPO (0.5 g) in 9.5 g of acetone,
slowly adding the BPO solution to the water-xanthan gum mixture, under rapid agitation over a period of 15-20 minutes to form a homogeneous suspension.

The MBPO-suspension was prepared in the same way, except that 0.5 MBPO was dissolved in 17 g methyl ethyl ketone (MBPO is not very soluble in acetone) and the final suspension was mixed for another 15-20 minutes at 40° C. in order to concentrate the suspension to 1 wt % MBPO.

The resulting suspensions were tested for their action on (ATCC 6538), *Staphylococcus epidermidis* (ATCC 12228), and *Propionibacerium acnes* (ATCC 6919) using the Time-Kill Procedure according to ASTM E2315.

The following testing parameters were used:

|  | *S. aureus* and *S. epidermidis*: | *P. acnes* |
| --- | --- | --- |
| Test Substance Vol. | 1 ml | 1 ml |
| Control Substance Vol. | 1 ml | 1 ml |
| Culture Growth Media | Tryptic Soy Broth (TSB) | TSA w/5.0% blood |
| Culture Growth Time | 18-24 hours | 144 hours (6 days) |
| Culture Dilution Media | Phosphate buffered saline (PBS) | PBS |
| Inoculum Vol. | 0.100 ml | 0.015 ml |
| Inoculum Conc. | ~1.0 × 10⁷ CFU/ml | ~1.0 × 10⁷ CFU/ml |
| Contact Temp | Ambient (25° C. ± 2° C.) | Ambient (25° C. ± 2° C.) |
| Contact Time | 30 minutes, 2 & 14 hours | 30 minutes, 2 & 14 hours |
| Volume Harvested | 0.100 ml | 0.100 ml |
| Neutralizer (Vol.) | D/E Broth supplemented with 0.1% catalase | D/E Broth supplemented with 0.1% catalase |
| Plating Media | Tryptic Soy Agar (TSA) | TSB w/5.0% blood |
| Enumeration Plate Incubation Temp. | 36° C. ± 1° C. | 36° C. ± 1° C. |
| Enumeration Plate Incubation Time | 48 ± 6 hours | 144 hours (6 days) |

Each test was duplicated.

Figure 2:
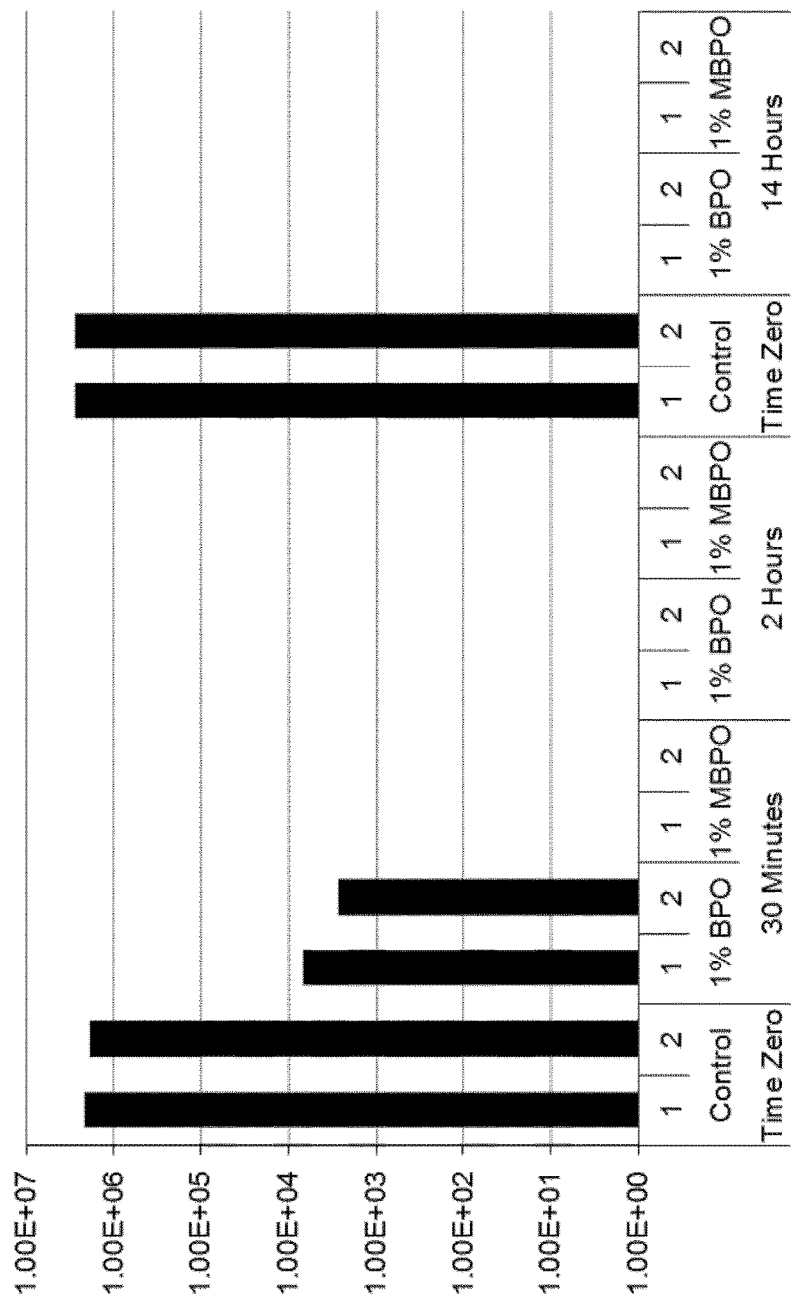

The number of colony forming units (CFU) per ml after 30 minutes, 2 hours, and 14 hours was determined in these tests and the results are displayed in FIGS. 1 (*S. aureus*), 2 (*S. epidermidis*), and 3 (*P. acnes*).

These figures show that di(4-methylbenzoyl) peroxide (MBPO) acts quicker on these bacteria than dibenzoyl peroxide (BPO).

The invention claimed is:

1. A method of treatment of acne comprising topical application to skin of an effective amount of peroxide of the formula

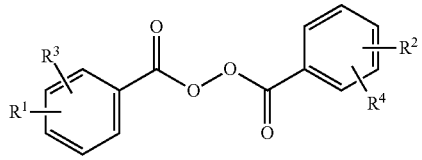

wherein $R^1$ is selected from linear and branched alkyl groups with 1-4 carbon atoms, and $R^2$, $R^3$, and $R^4$ are selected from hydrogen and linear and branched alkyl groups with 1-4 carbon atoms.

2. The method of claim 1 wherein $R^1$ and $R^2$ are selected from methyl, tert-butyl, and n-butyl groups.

3. The method of claim 1 wherein $R^3$ and $R^4$ are both hydrogen.

4. The method of claim 3 wherein $R^1$ and $R^2$ are positioned at the para position.

5. The method of claim 1 wherein the peroxide is di(4-methylbenzoyl)peroxide.

6. A method of inhibiting the proliferation of *Staphylococcus aureus*, *Staphylococcus epidermidis*, and/or *Propionibacerium acnes* to a subject in need thereof; comprising the topical application of an effective amount of a peroxide with the formula

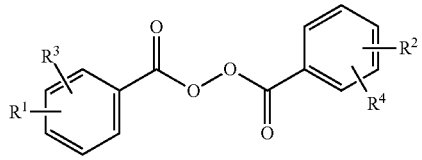

wherein $R^1$ is selected from linear and branched alkyl groups with 1-4 carbon atoms, and $R^2$, $R^3$, and $R^4$ are selected from hydrogen and linear and branched alkyl groups with 1-4 carbon atoms.

7. The method of claim 6 wherein the peroxide is di(4-methylbenzoyl)peroxide.

* * * * *